US008916356B2

(12) United States Patent
Hemker et al.

(10) Patent No.: US 8,916,356 B2
(45) Date of Patent: Dec. 23, 2014

(54) MEASURING THROMBIN ACTIVITY IN WHOLE BLOOD

(75) Inventors: Hendrik Coenraad Hemker, Maastricht (NL); Suzette Beguin, Villers-Agron (FR); Raed Al-Dieri, Maastricht (NL); Robert Wagenvoord, Maastricht (NL); Sebastiaan Nijhuis, Maastricht (NL); Peter Giesen, Maastricht (NL)

(73) Assignee: Synapse B.V., Maastricht (NL)

( * ) Notice: Subject to any disclaimer, the term of this patent is extended or adjusted under 35 U.S.C. 154(b) by 1539 days.

(21) Appl. No.: 11/919,431

(22) PCT Filed: Apr. 26, 2006

(86) PCT No.: PCT/EP2006/004945
§ 371 (c)(1),
(2), (4) Date: Aug. 7, 2008

(87) PCT Pub. No.: WO2006/117246
PCT Pub. Date: Nov. 9, 2006

(65) Prior Publication Data
US 2009/0311730 A1     Dec. 17, 2009

(30) Foreign Application Priority Data

Apr. 29, 2005   (EP) .................................... 05290952

(51) Int. Cl.
*C12Q 1/56*   (2006.01)
(52) U.S. Cl.
USPC ......................................................... 435/13
(58) Field of Classification Search
None
See application file for complete search history.

(56) References Cited

U.S. PATENT DOCUMENTS 4,292,272 A * 9/1981 Kitajima et al. .............. 422/428

FOREIGN PATENT DOCUMENTS

WO         93/22453 A1    11/1993
WO         03/093831 A1   11/2003

OTHER PUBLICATIONS

Valenzano et al., "Development of a Fluorescent Ligand-Binding Assay Using the Acrowell Filter Plate", Journal of Biomolecular Screening, 2000, vol. 5, No. 6, pp. 455-461.*
Yingyongnarongkul et al., "Parallel and Multiplexed Bead-based Assays and Encoding Strategies", Combinatorial Chemistry and High Throughput Screening, 2003, vol. 6, pp. 577-587.*

H.C. Hemker, et al., "The Thrombogram: Monitoring Thrombin Generation in Platelet Rich Plasma," Thrombosis and Haemostatis, XP9000027, Apr. 2000, pp. 589-591, vol. 83, No. 4.
H.C. Hemker, et al., "The Calibrated Automated Thrombogram (CAT): A Universal Routine Test for Hyper- and Hypocoagulability," Pathophysiology of Haemostatis and Thrombosis, XP008053801, 2002, pp. 249-253, vol. 32, No. 5/6.
H.C. Hemker, et al., "Calibrated Automated Thrombin Generation Measurement in Clotting Plasma," Pathophysiology of Haemostasis and Thrombosis, XP008053802, Jun. 2003, pp. 4-15, vol. 33, No. 1.
S.J.H. Wielders, et al., "Factor Xi-Dependent Reciprocal Thrombin Generation Consolidates Blood Coagulation When Tissue Factor is Not Available," Arteriosclerosis, Thrombosis and Vascular Biology, XP-002379074, Jun. 2004, pp. 1138-1142, vol. 24, No. 6.
K. Vanschoonbeek, et al., "Initiating and Potentiating Role of Platelets in Tissue Factor-Induced Thrombin Generation in the Presence of Plasma: Subject-Dependent Variation in Thrombogram Characteristics," Journal of Thrombosis and Haemostasis, XP-002396291, Mar. 2004, pp. 476-484, vol. 2, No. 3.
Y. Dargaud, et al., "Inherited Bleeding Disorder Due to Familial Type 2 Platelet Cyclo-Oxygenase Deficiency," Thrombosis Research, Mar. 16, 2005, pp. 483-489, vol. 116, No. 6.
K. Tanaka, et al., "Thrombin Generation Before and After Cardiopulmonary Bypass," Anesthesiology Abstracts of Scientific Papers Annual Meeting, XP-002396292, No. 2003, 2003, pp. Abstract No. A-158.
Y. Dargaud, et al., "Evaluation of Thrombin Generating Capacity in Plasma From Patients with Haemophilia A and B," Thrombosis and Haemostasis, XP-002396293, Mar. 2005, pp. 475-480, vol. 93, No. 3.
T. Furugohri, et al., "Different Antithrombotic Properties of Factor Xa Inhibitor and Thrombin Inhibitor in Rat Thrombosis Models," European Journal of Pharmacology, Apr. 2005, pp. 35-42, vol. 514, No. 1.
N. Fuchi, et al., "The Synthesis of Beta-Strand Mimetic Templates via Regioselective 1,3-dipolar Cycloaddition with Vinylsulfone," Tetrahedron Letters, Feb. 2001, pp. 1305-1308, vol. 42, No. 7.
Anonymous: "Fluoroskan Ascent," Thermo Electron Corporation, Jan. 4, 2004, XP-002349946, url: http://www.thermo.com/com/cda/product/detail.
Microplate Dimensions Summary Chart (cited in Office Action dated Feb. 9, 2012, issued in corresponding Indian application), http://www.perkinelmer.com/CMSResources/Images/44-73879SPCMicroplateDimensionsSummaryChart.pdf.

* cited by examiner

*Primary Examiner* — Ralph Gitomer
(74) *Attorney, Agent, or Firm* — Sughrue Mion, PLLC

(57) ABSTRACT

The invention relates to a method for in vitro determining thrombin activity in a sample wherein the sample is a blood sample and thrombin generation is measured by the steps of: —contacting a layer of said sample with a fluorogenic substrate of thrombin, wherein said layer has a thickness within a range of 0.05 to 5 mm and a surface within a range of 10 to 500 mm2; —allowing thrombin to generate in said sample; —measuring the fluorescence emitted from the surface of the layer, by the fluorescent group released from the fluorogenic substrate as a result of enzymatic action of generated thrombin on said fluorogenic substrate.

28 Claims, 13 Drawing Sheets

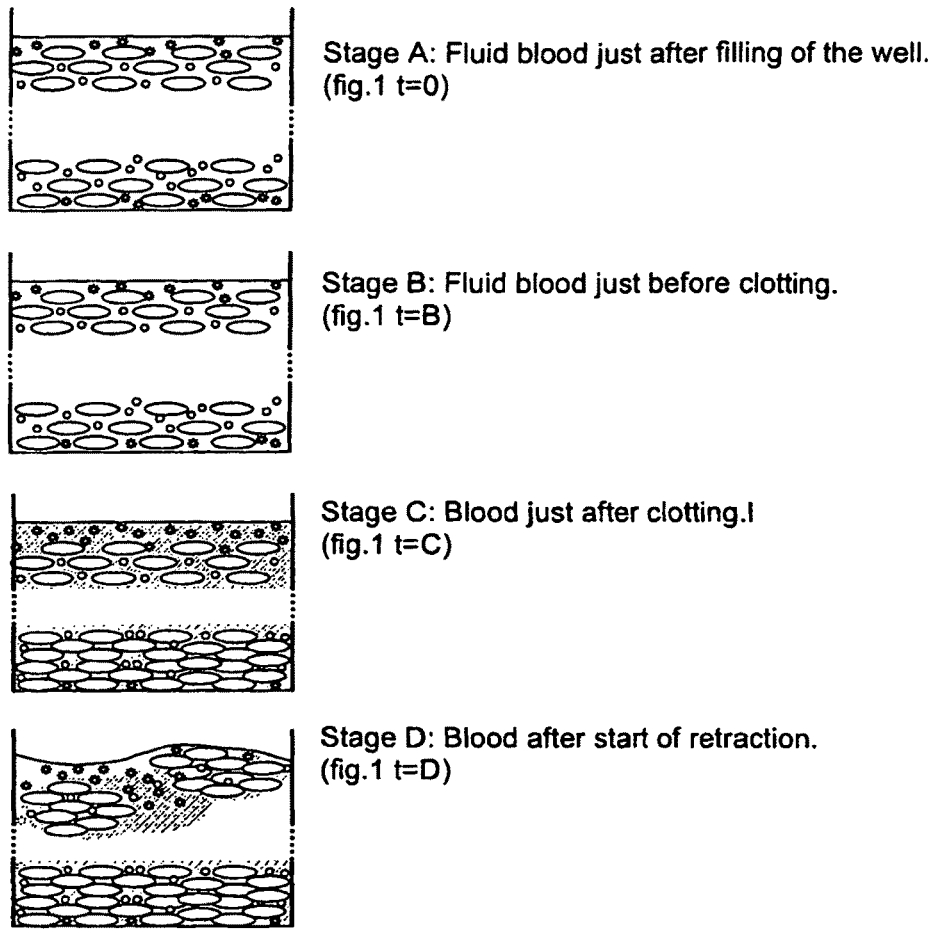

Figure 1:
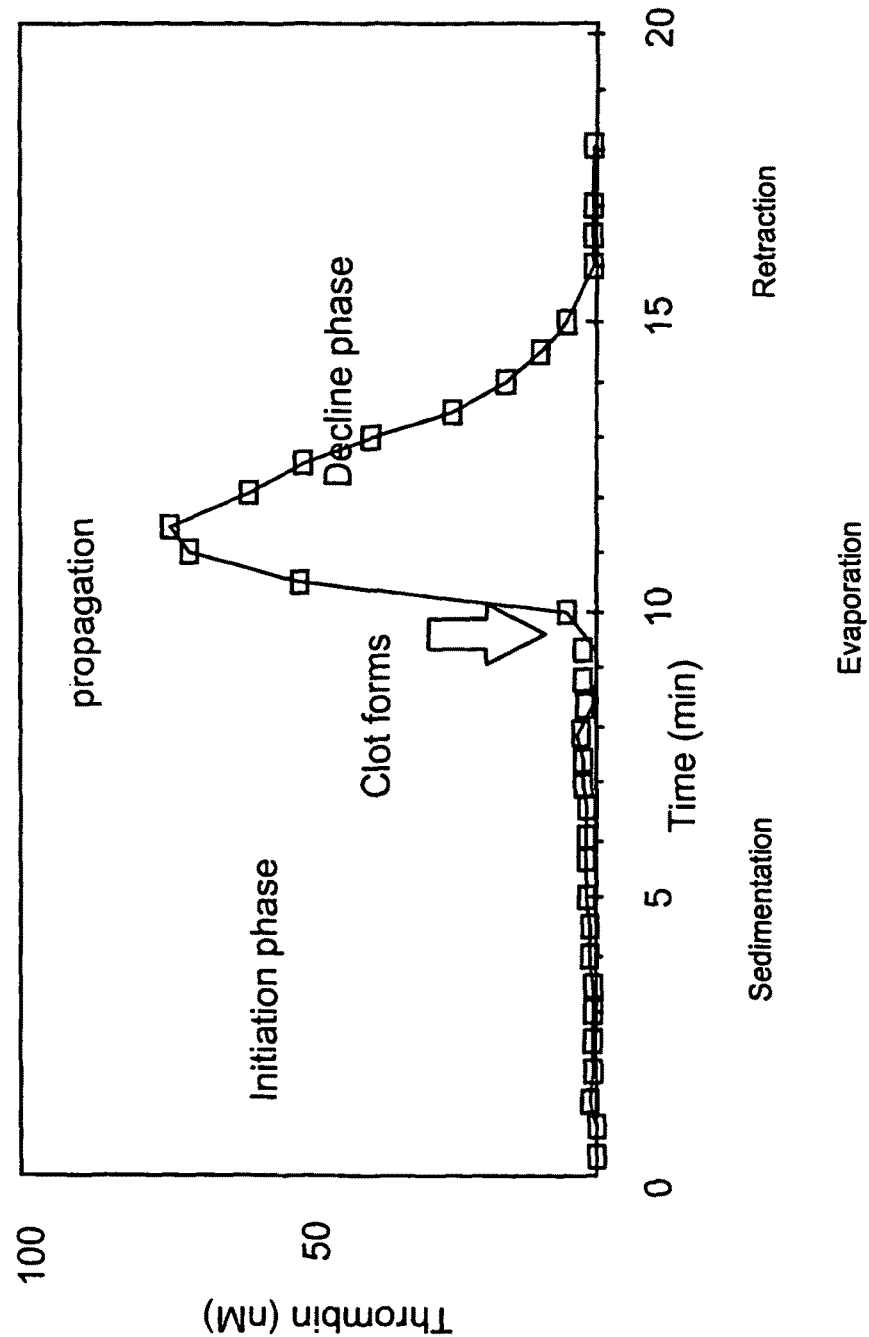

Figure 4
*Schematic representation of the effects of sedimentation and clot retraction on the fluorescent signal from cloting whole blood*
Legend:
    Large ovals: Red blood cells
    Starred circles: Fluorescent molecules that are exitated
    Square: Fluorescent molecules that are not exitated
    Top horizontal (c.q. curved-) line: fluid surface
    Bottom horizontal line: transparent bottom of measuring well

Figure 4

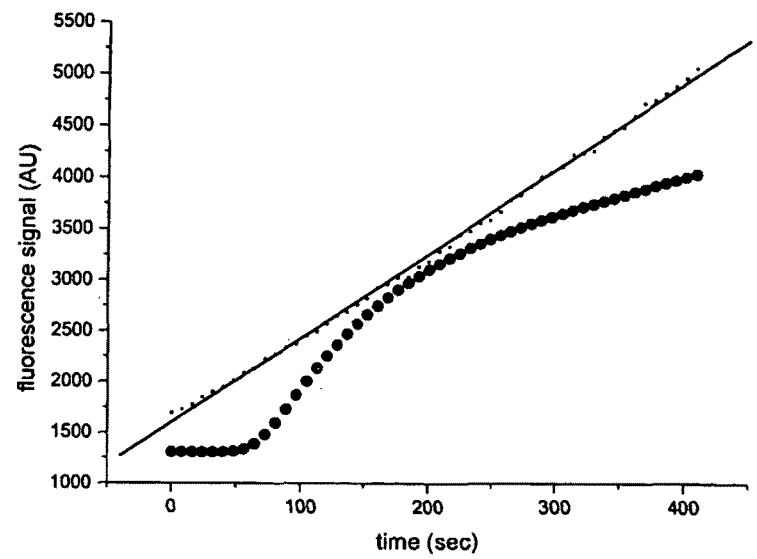
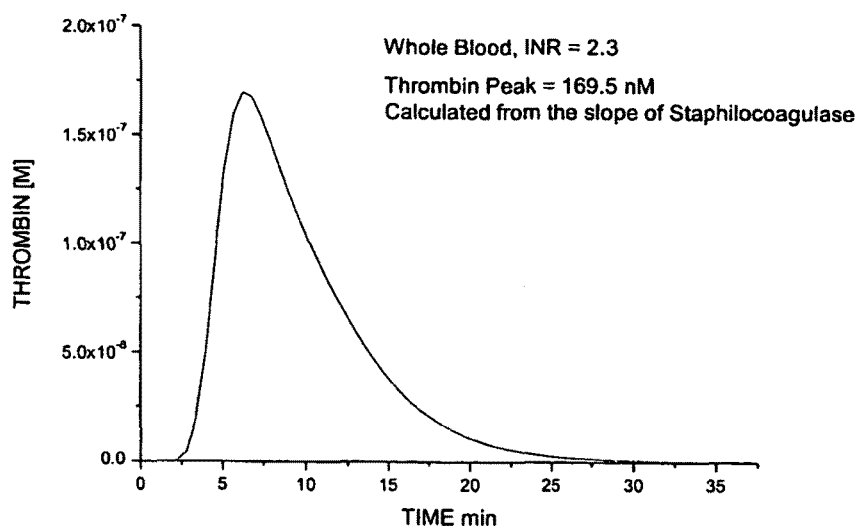
Figure 12

MEASURING THROMBIN ACTIVITY IN WHOLE BLOOD

CROSS REFERENCE TO RELATED APPLICATIONS

This application is a National Stage application filed under Rule 371 based on PCT/EP2006/004945 filed Apr. 26, 2006, which claims priority to EP 05290952.0 filed Apr. 29, 2005.

The invention relates to a method of determining, especially measuring the time course of thrombin activity in vitro, i.e., measuring active thrombin in a sample, especially as it develops in a clotting sample consisting of whole blood. The result of measurement of thrombin activity can be represented by the so-called "thrombin generation curve" illustrated in FIG. 1.

The invention also relates to means enabling the measurement of active thrombin following its generation in a sample in vitro. It is also directed to the use of said method of measurement for the detection or the monitoring of the condition of a patient, including for detection or monitoring of a pathological condition related to blood coagulation deficiency.

The invention also concerns the use of the method of measurement for the screening of substances, including for the screening of drugs which could interact with the coagulation process, especially with thrombin activity.

Thrombotic diseases, such as coronary infarction, stroke, pulmonary embolism and several others are responsible for about half of all death and disability in western society. In developing countries they increase with the degree of development. Bleeding disease, although numerically less important, are also a significant cause of death. Thus over- or under-function of the haemostatic system is an extremely important pathogenetic mechanism. It therefore is all the more surprising that a good clinical function test is not available.

The Role of Thrombin in Haemostatic and Thrombotic Disease:

In haemostasis and thrombosis thrombin plays a pivotal role. In venous thrombotic disease this has long since been recognized (1) and is convincingly demonstrated by the fact that prevention and treatment of venous thrombosis is best brought about by decreasing thrombin activity, either by direct inhibition (hirudin, melagastran) or by decreased synthesis (vitamin K antagonists) or by increased decay (heparins). In the last decennia it became increasingly clear that thrombin is as important in arterial disease as it is in venous disease. Clinical trials have shown that vitamin K antagonists (2) as well as heparin (3) decrease the reoccurrence rate of myocardial infarction. A role for thrombin in bleeding is suggested by the prolonged bleeding time seen when thrombin generation is as profoundly affected as in severe overdosage of oral anticoagulants (4) or heparin (5). Also, the haemophilias are diseases of the thrombin forming system (6).

All Elements of the Blood Participate in Thrombin Formation:

Modern research has led to the recognition that thrombin is formed through the cooperation of the formed elements of the blood and plasma. Red blood cells (RBCs) are the least active in this respect although in a small percentage of them the outer membrane exhibits procoagulant activity (7). Much more important is that white blood cells carry tissue factor activity. This activity normally is encrypted but in lesion becomes manifest through interactions with blood platelets (8,9). The main players are undoubtedly the platelets and the plasmatic clotting system. In textbooks it is still found that platelets are responsible for primary haemostasis and arterial thrombosis whereas the clotting of plasma serves for consolidation of the haemostatic plug and is the mechanism behind venous thrombosis. This view is due to the fact that plasma and platelets were studied apart from each other. In reality the cooperation between platelets and plasma and the other cells of the blood is essential in both primary and secondary haemostasis and in arterial and venous thrombosis. Platelet plug formation plays a role in thrombin generation because the interstices in a platelet aggregate form an unstirred niche in which thrombin can form without being swept away by flowing blood. That is why measuring thrombin generation in clotting whole blood is so close to physiological reality.

Apart from forming a "sponge" in which thrombin can form, platelets also actively contribute to the generation of thrombin. They shed factor V and provide the procoagulant phospholipid surface required for prothrombin conversion as well as for the different steps in the coagulation mechanism that lead to prothrombinase formation (10). The velocity of thrombin generation and the amount formed thus depends upon platelet activity as well as on the plasma proteins involved. Particularly interesting is the role of polymerizing fibrin. Von Willebrand factor (vWf) interacts with polymerizing fibrin and undergoes a conformational change which makes it reactive to platelet receptor GPlb and through this binding cooperates to the platelet becoming procoagulant (11,12). This shows that forming a fibrin clot is not the closing act of haemostatis and that thrombin formation in a plug (or thrombus, or clot) is a key event in the process. Indeed, as we will see below, >95% of all the thrombin formed is formed after clotting has taken place and this thrombin is essential in the haemostasis and thrombosis (H&T) process. Perhaps the best proof of the tight bonds between platelets and the plasmatic clotting system is the fact that all "aggregation inhibitors" and other antiplatelet agents also inhibit thrombin generation in platelet rich plasma (or whole blood). This has been shown for aspirin (13), abciximab (14), MK383 (15) and clopidogrel (16). Inversely, the fact that the antiplatelet drug par excellence, aspirin, prevents venous thrombosis (17) further illustrates the close connection between platelet function and blood coagulation.

So, in summary, the amount of thrombin formed in a clot is an essential feature in the process of haemostatis and thrombosis and all the elements of blood take part in its formation.

Thrombin Generation (TG) as an Indicator of Thrombotic- and Bleeding Risk:

Increased TG invariably indicates thrombotic risk, whether it is due to deficiency of antithrombin or an excess of prothrombin. Also in disorders in the protein C pathway (deficiency of proteins S and C, factor $V_{Leiden}$) thrombin generation is higher than normal. This holds for plasma clotting as such, but becomes especially obvious if the protein C pathway is activated by thrombomodulin (FIG. 1). The thrombotic tendency induced by oral contraceptives can be attributed to an acquired resistance to activated protein C which causes a 10% increase of thrombin generation which becomes more obvious when TM or APC is added (18,19).

A particularly interesting case is the lupus anticoagulant. This type of antibody induces an increase of the lag time of thrombin formation, and therefore an increase of clotting time, but also an important resistance to the activity of the protein C system (20). This explains the "LE paradox" i.e. an anticoagulant effect that is accompanied by a thrombotic tendency.

Excess amounts of factors II, VIII and VII have been found to correlate with the occurrence of myocardial infarction (21-24). Also higher than normal levels of vWF increase thrombin generation (12) are a risk factor for arterial thrombosis (25,26).

In a sub-population of young stroke patients (around 30%) both thrombin generation in Plasma Rich Platelet (PRP) and vWF have been shown to be significantly higher than normal (27). In all congenital coagulation factor deficiencies thrombin generation is decreased. This has been demonstrated for the haemophilias A, B and C (deficiency of factor VIII, IX or XI; 28-31) as well as for all rare deficiencies (prothrombin, factors V, VII, X, XII; 32). A bleeding tendency is seen as soon as TG is below 20% of normal. In haemophilia A not only infusion of factor VIII or administration of DDAVP augments the capacity of blood to form thrombin but also inhibitor bypassing therapy with products containing prothrombin and/or factor VII increases thrombin generation.

Severe thrombopenia (<50 000 µl−1) causes decreased thrombin generation as well as the Glanzman and Bernard-Soulier thrombopathies. In von Willebrand's disease—hitherto known to induce a disorder of platelet adhesion at high shear rates—thrombin generation in platelet rich plasma is significantly impaired (see above). The defect in PRP is much higher than in Plasma Poor Platelet (PPP), which indicates that it cannot be explained by the concomitant—usually mild—decrease of factor VIII.

The Thrombogram

The following remarks should be taken into consideration with respect to the mechanism of thrombin generation when addressing the problem to be solved according to the invention.

Even a simplified scheme of the mechanism of thrombin formation (FIG. 1) shows that it is extremely complex and replete with positive and negative feedback reactions. Indeed so complex as to become a non-linear system, i.e., there are no simple relations between the concentration of the reactants and the outcome and threshold phenomena may cause the system to react essentially unpredictably. The reaction of the whole to a given trigger can therefore not be deduced from knowledge of the individual concentrations of the relevant reactants (that may not even be known) and only a test that measures the function of the complete system as contained in the blood of a patient reveals the haemostatic/thrombotic status of that patient.

The result of the whole process of thrombin generation is the appearance and disappearance of a transient thrombin activity. The curve of thrombin activity against time, or Thrombogram™ (TG) is characterised by an initiation phase, or lag-time, during which only minute amounts of thrombin are formed; then follows a burst of activity, known as the propagation phase (FIG. 1). Blood forms a clot at the very beginning of the burst and almost all thrombin is formed after the clot has formed. All formed thrombin is subsequently inactivated by the antithrombins of the blood. These proteins bind stoichiometrically to thrombin in a slow reaction. The inactivation velocity is proportional to the concentration of thrombin and of antithrombin. As long as the conversion rate of prothrombin is higher than the inactivation rate of thrombin the level of thrombin increases. As the level of thrombin increases the inactivation rate also increases. At the peak both velocities are equal, thereafter decay predominates. The obtained curve of thrombin activity shows the various phases and especially shows the peak of thrombin generation, the time to reach the peak and the endogenous thrombin potential (ETP).

PRIOR ART

The necessity to measure the function of the haemostasis and thrombosis system has not escaped the attention of the medical profession over the last century. Solutions to this problem have essentially not changed until the 1990ies, offering means that were either practical but inadequate or adequate but impractical.

The practical solutions relate to the measurement of the clotting time and the bleeding time. The clotting time measures the length of the initiation phase of thrombin generation and therefore reflects only part of the function (33, see also above). The sole fact that many varieties of the test are in use in the clinical laboratory, each useful in a specific situation only, already shows that a clotting time does not reflect the coagulation mechanism as a whole. For the bleeding time it can be said that it is extremely imprecise having a coefficient of variation around 40%, which strongly limits its practical use (34).

Since the 1950ies it has been recognized that measuring the time course of thrombin in clotting blood is the best to estimate H&T function (35-37). Until 1992 the only way to measure the TG was by taking samples from clotting blood or plasma and determining the thrombin content therein. This takes one man-hour per curve and thus can be suitable for research purposes but not for modern clinical and epidemiological use.

In the 1990 Hemker and Béguin et al. (EP-B1-0 420 332) launched the idea of adding to the clotting blood a chromogenic (colour producing) substrate having high specificity for thrombin but a low turnover rate (low $K_{cat}$) and little binding affinity for thrombin (high Km). Such a substrate remains present during the whole process of TG and the sum (i.e. the integral) of the thrombin activity over time can be measured from the total amount of product formed. Ideally this measures the Endogenous Thrombin Potential (ETP), i.e. the Area Under the thrombin generation (AUC).

Later, Hemker et al. further developed this method to obtain the whole of the TG curve (38). This was based upon the principle that, if the kinetic constants of the substrate are favourable, the reaction velocity can, in good approximation, remain proportional to the thrombin concentration during the whole of the coagulation process, so that the first derivative of the product concentration gives a curve that is proportional to the thrombin activity. This method, described in WO 03/093831 A1, was an extension and elaboration of the procedure earlier disclosed in EP-B2-0420332, where only the end-level of product is measured, in which way the area under the curve of the TG, i.e. the ETP is obtained.

The substrates used in this method yield a yellow product, the monitoring of which requires measuring optical density and therefore an optically clear reaction medium. The turbidity caused by the clotting of fibrinogen has therefore to be avoided and fibrinogen has either to be removed or its polymerisation has to be prevented by adding polymerisation inhibitors. Removal of fibrinogen has however the disadvantage of removing an important reactant and cannot be carried out without removing cellular elements such as the important blood platelets. Furthermore, addition of polymerisation inhibitors, at the high concentrations required to prevent fibrin formation completely, inhibit the prothrombin converting enzyme and the biochemical reactions leading to its formation.

In contrast to optical density, fluorescence can be measured in turbid media. Unlike chromogenic substrates, substrates that yield a fluorescent product (fluorogenic substates) can therefore be used in plasma that is not defibrinated and therefore also in Platelet Rich Plasma (PRP) (33, 39-43). The use of a fluorogenic substrate introduces two important disadvantages however: 1) fluorescence intensity is not proportional to the concentration of the fluorophore because of the so-called inner filter effect; 2) with the available substates the rate of product formation is not necessarily proportional to the enzyme concentration. The latter disadvantage can be overcome by using substrates that are not significantly consumed, as in the chromogenic method. Such substrates at the moment are not available. In actual practice at this moment both problems are solved together by continuous comparison of the experimental signal to that of a constant thrombin-like activity acting under exactly identical conditions as those in the measured sample (WO 03/093831 A1).

Figure 2:
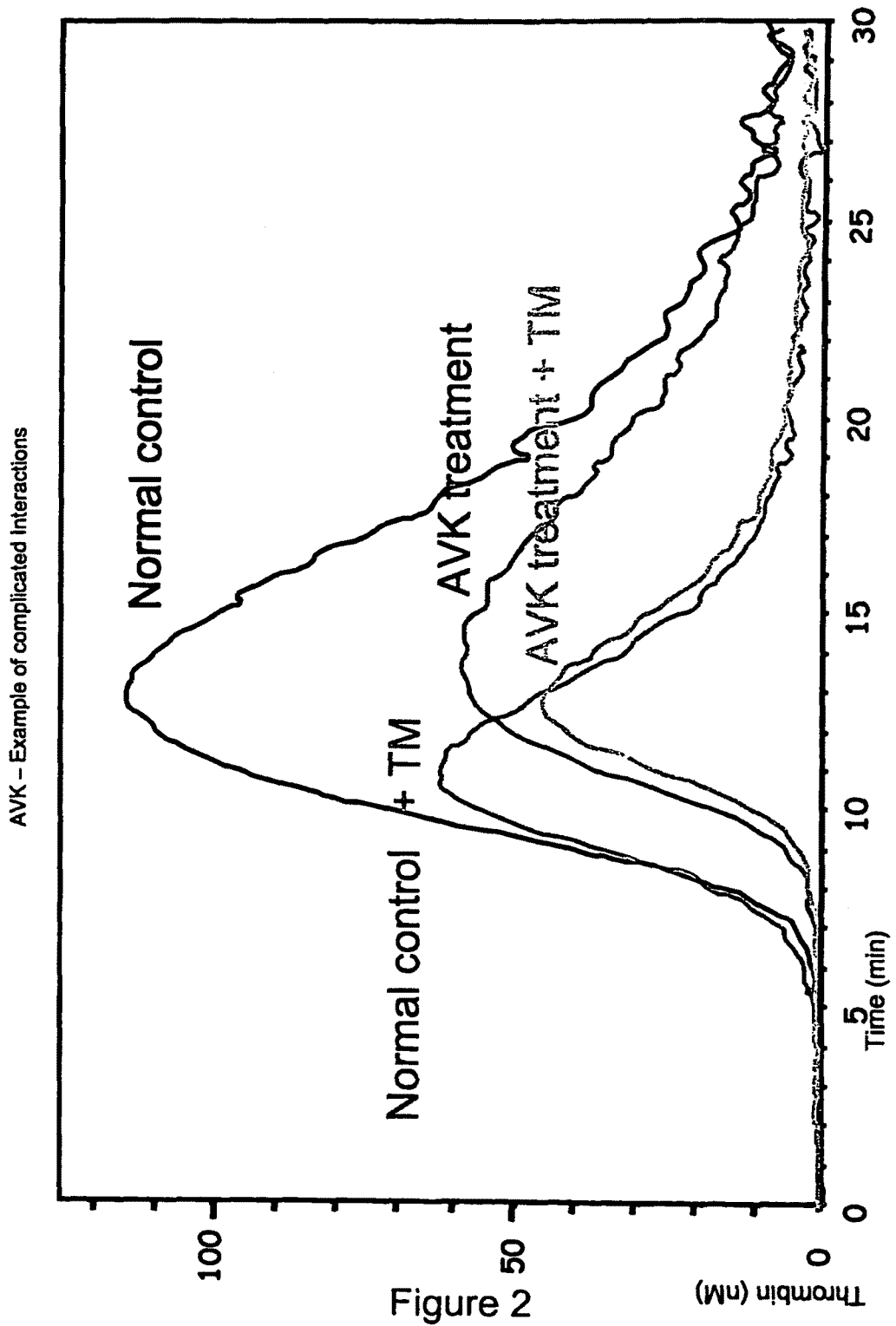

The chromogenic method can obviously not be used with whole blood because blood is not translucent. Fluorogenic substrates have been reported to be applicable to measure TG in whole blood (44). In actual practice this published method more often than not yields erratic signals that do not resemble the course of thrombin generation as it is known from the established subsampling method (FIG. 2). Also the quantitative relation between the signal obtained and the amount of thrombin present varies from experiment to experiment. In short, the method described does not yield reproducible and quantifiable results.

Another possibility is the strong dilution of the blood (10-fold or more), so that the red blood cells RBC have less influence (45). This yields curves that are indeed better than those which are obtained minimally diluted blood. This approach cannot however be thought to represent the physiological situation for two reasons. In the first place, after forming a clot (i.e. during the most important phase of thrombin generation), the thrombin forming reactions are diffusion limited because they take place at insoluble interfaces (surface of platelets and other cells immobilised in the fibrin network). This makes them more sensitive to dilution than the reactions in free solution such as the thrombin inactivation reactions. In diluted blood the equilibrium between thrombin forming and thrombin inactivating reactions therefore is not representative for the situation existing in vivo. This is even more important in the case that pathological inhibitors are contained in blood (e.g. in therapy refractive haemophilia or lupus erythematodes inhibitor). It is well known in clinical practice that coagulation inhibitors loose their effect upon dilution in vitro.

Hence the problem remains of how to obtain a signal from which the changing thrombin concentration can be determined in a sample of clotting blood that is less than ten times diluted. The present invention intends to provide a solution to this problem which overcome at least some of the drawbacks faced in the prior art.

It was found by the inventors that the irreproducible and erratic results obtained before the present invention, were at least due to two causes; a: sedimentation before the blood clots and b: retraction of the clot after clotting has taken place (see FIG. 4). It follows therefrom that the volume from which fluorescence is obtained changes during the reaction and that the geometric form of the surface changes, causing erratic focussing and reflection of light that disturbs the signal recovered. Unexpectedly it was found by the inventors that these phenomena do not occur when operating on a thin layer of blood and especially on a thin layer provided with a grid and/or with microbeads. The geometric form of a thin layer, together or not with said grid and/or microbeads, indeed prevents sedimentation and retraction. The reaction volume however remains unknown, hence it has to be determined during the experiment. This is done by adding, at the start of the experiment, a known concentration of a fluorescent molecule. The signal is small and thus the signal to noise ratio is advantageously increased by measuring over a large surface area with any appropriate device known to the art. Furthermore, as large volume-to-surface ratios tend to evaporation, suitable measures to prevent this should advantageously be taken.

According to the invention, a method is described which is a method for in vitro determining the course of thrombin activity in time in a sample wherein the sample is a blood sample and thrombin generation is measured by the steps of:
   contacting a layer of said sample with a fluorogenic substrate of thrombin, wherein said layer has a thickness within a range of 0.05 to 5 mm and a surface within a range of 10 to 500 mm$^2$;
   allowing thrombin to generate in said sample;
   measuring the fluorescence emitted from the surface of the layer, by the fluorescent group released from the fluorogenic substrate as a result of enzymatic action of generated thrombin on said fluorogenic substrate.

The method of determining thrombin activity enables measurement of the time course of the concentration of thrombin as it results from its formation and subsequent inactivation, according to the coagulation scheme.

The method of the invention can be carried out on blood sample such as samples of whole blood or Platelet Rich Plasma (PRP) sample.

Thrombin is allowed to generate in the sample usually after the contacting of said sample, with components suitable for initiation of thrombin generation. Such components can comprise clotting factors such as tissue factor, and possibly calcium ions.

While thrombin is generated and present in the reaction mixture (active thrombin), it reacts with its fluorogenic substrate, with the result that the fluorescent group of the substrate is released.

The reaction is designed in such a way that the fluorogenic substrate is present during the whole duration of the reaction, in high enough amounts to allow measuring thrombin activity. For example, the substrate concentration is around or above the Km of the substrate for thrombin, so that the consumption of the substrate has not much influence on the reaction velocity. The substrate is converted by thrombin, leading to an increase of the fluorescence emitted from the surface of the assayed sample.

The method defined in the invention, enables thrombin generation to take place in a blood sample, especially in a whole blood sample, in a way which is essentially comparable to the thrombin generation which occurs in the body. It therefore provides a reliable method of measurement for application in haemostasis and thrombotic studies.

The step of measuring the increase of the fluorescence emitted from the surface of the layer of the assayed sample, as a result of the release of the fluorescent group from the substrate through thrombin action, is carried out especially using an optical device that both allows to illuminate large surfaces, such as surfaces having from 10 to 500 mm$^2$ and that allows to collect the emitted light from that surface. The wavelength selected for the measurement of the fluorescence is determined by the selected fluorescent group. One wavelength is determined for the excitation light which is delivered to the sample to proceed with the measurement. Another wavelength is determined for the emitted light resulting from the release of the fluorescent group of the fluorogenic substrate of thrombin. An optical device, such as a fluorescent plate reader known to persons skilled in the art (e.g. the Ascent Fluorescent plate reader, Thermolabsystems) is suitable to measure the fluorescence.

According to an embodiment of the invention, the sample to be assayed, especially the whole blood sample, is filled in one or more containers allowing advantageously to carry out several samples to be assayed at the same time. Such containers are designed to enable the sample to be filled in, according to the defined conditions of thickness and surface of the layer of sample to be analyzed. E.g. flat bottom microplates containing wells or a container or support having another suitable geometric design, known by the skilled person in the field of such analysis can be used.

Other devices can be used as support for the samples if they fulfil the requirement of enabling said samples to be provided for the analysis as a layer complying with the definitions of the invention. Therefore, the description of the method and means of carrying out the invention, which is made by reference to wells (of microplates) containing the samples can apply to other devices (container or support) containing the samples.

According to the method of the invention, the concentration of thrombin during the assay is a function of the measured fluorescence of the released fluorescent group of the fluorogenic thrombin substrate. It is especially proportional to the increase rate of the fluorescence appearance.

Accordingly, the method of the invention enables the measurement of thrombin concentration during the whole time of thrombin activity in the sample, provided the fluorogenic substrate is present in appropriate quantities.

Therefore, the course of thrombin activity, before and after clotting of the blood, up to the peak of thrombin and also during decrease of thrombin concentration after the thrombin peak has been obtained as a result of thrombin inactivation, is represented by a measurement of the time-dependent thrombin concentration curve. During the various steps of thrombin activity, the fluorogenic substrate reacts with the thrombin which is present and is especially hydrolyzed, resulting in the release of the fluorescent group.

A particular advantage of the invention is that the method enables measurement of thrombin generation in a sample, especially in a whole blood sample which is not diluted or which is minimally diluted, within a range of maximum ten times, especially less or equal to 4 times.

In a particular embodiment of the described method, the thickness of the layer of sample to be analysed, especially of whole blood is from 1 to 3 mm, especially about 2 mm or less.

In a particular embodiment of the method, the surface of the sample, especially of the whole blood sample, when it is filled in the wells of the microplate or any appropriate container or support, is larger than 20 mm$^2$ for example from 30 mm$^2$ to 200 mm$^2$, especially larger than 100 mm$^2$, in particular within a range of 150 to 200 mm$^2$ As an example, the sample is filled in wells of microplates, each well having a diameter of 15 mm and the thickness of the blood sample is less than 2 mm, enabling measurement on a surface of about 175 mm$^2$.

The measurement of thrombin activity is performed in a way that enables multiple lecture points of the fluorescence at the surface of each sample.

According to an embodiment of the invention, the method is carried out with a sample, especially a whole blood sample which is filled in the wells of a plate or other container or support wherein said wells also contain a grid especially with a mesh size of 50 μm.

Alternatively or in addition to such grid in an embodiment of the invention, the sample, especially the whole blood sample, is filled within a well of a plate or other container or support which contains microbeads.

The presence of either said grid and/or microbeads is advantageous to help dispersion of the blood in the well and especially to prevent retraction of the clot in the clotting blood. In other words, the presence of the grid or microbeads can prevent disturbances of the surface of the clotting blood that blur the signal which is measured during thrombin activity. Such grid and/or microbeads can improve the attenuation of retraction effects which is obtained by using a large surface for measurement. Other means enabling said effect can also be used.

In a particular embodiment of the invention, the wells containing the sample, especially the whole blood samples are covered to avoid drying of the blood during time of measurement of thrombin activity, as a result of evaporation. Such covering can be performed with usual materials, such as types of thin plastic film, provided they do not interfere with fluorescence measurement.

The measurement of the thrombin activity in the blood sample is carried out from the time where the sample is filled within the wells (or any other appropriate device such as a slit) and required components to initiate thrombin generation are provided to said sample, including tissue factor, up to the time where thrombin has been consumed in the coagulation process.

In a particular embodiment of the method of the invention, the amount of thrombin fluorogenic substrate added to the sample is within a range of 50-1000 μM. According to the disclosed method, in order to be able to know the concentration of active thrombin in absolute terms (i.e. in nM/L), it is necessary to know the volume of the blood sample within which the measurement of fluorescence is carried out. To this end a known concentration of a fluorophore can be added to the fluorogenic substrate of thrombin wherein the respective proportions of thrombin substrate to fluorophore is in the range of 1% to 10% of the quantity of the fluorescent molecule bound to thrombin substrate, especially in the range of 1% to 5%.

In a particular embodiment of the invention, the fluorophore is of the same nature as the fluorescent molecule which is released by the action of thrombin upon the fluorogenic substrate.

In another embodiment this fluorophore is a different species than the fluorescent molecule of the fluorogenic substrate. In this case, the measurement of fluorescence takes into account the presence of this new species of fluorophore; it especially includes the measurement of the fluorescence of the fluorophore.

The addition of a known concentration of such a fluorophore provides an internal standard in the sample to be analysed and allows the assessment of the volume of the sample wherein fluorescence is actually measured.

In order to carry out the method of determining thrombin generation in a sample especially a whole blood sample, a synthetic substrate for thrombin which consists of an organic chemical coupled with the fluorescent molecule is advantageously used.

The synthetic fluorogenic substrate can be an oligopeptide having the sequence of 2 to 30 amino acid residues coupled with a fluorescent molecule.

It can be especially useful that the fluorogenic group is bound to a terminal lysine or arginine residue in the substrate because thrombin splits preferably groups bound to these amino acid residues.

According to a particular embodiment, the fluorescent molecule used is AMC (7-amino-4 methylcoumarin) or p-nitroanilide. Synthetic substrates have been described by Rijkers, D. T., H. C. Hemker, et al (1996), Int J Pept Protein Res 48(2): 182-93; Rijkers, D. T., S. J. Wielders, et al (1995), Thromb Res 79(5-6): 491-9; Wielders, S. M. Mukherjee, et al (1997), Thromb Haemost 77(4): 629-36.

A particular synthetic fluorogenic thrombin substrate suitable to perform the invention is Z-Gly-Gly-Arg-AMC (available from BACHEM).

In a particular embodiment of the invention, the wells (or any other appropriate device) containing the sample can further comprise a gel, possibly a gel containing calcium ions, said gel being prepared so that it does not enable dilution of the whole blood of the sample. Gel such as Sefadex or agarose gels can be used to the extent that they are not dried in such a way that they would allow liquid of plasma to go in to the gel.

When a gel is used, it can be filled in the wells prior or together with the whole blood sample.

The compounds which can be added to the sample in order to allow thrombin generation comprise tissue factor and calcium ions, which compounds are added in quantities enabling coagulation to start.

Such quantities can be within the range of 0.05 picomole/L to 15 nanomole/L for tissue factor, and around 10 mM of $Ca^{++}$-ions when citrated blood is used. The invention explicitly also covers the case where native, non anticoagulated blood is used, in which case no $Ca^{++}$ needs to be added. Alternatively, in certain applications it is profitable not to add tissue factor in order to investigate the spontaneous coagulability of the blood. The tissue factor, when needed, is added just before starting the measurement.

Calcium ions and/or fluorogenic substrate can be added either directly with the blood sample especially when calcium and fluorogenic substrate are used in a solution. Tissue factor can also be added alternatively to the blood sample.

When the sample and various compounds are filled into the well, the measurement is immediately carried out.

In a particular embodiment of the method of the invention, the whole blood which is assayed is citrated blood.

The method of measurement of thrombin activity in the whole blood sample can be advantageously used for detecting or monitoring a haemostatic disease or a thrombotic disease or for detecting or monitoring the possibility that such a disease appears in a patient.

The method also enables the detection or monitoring the interaction of determined substance(s) on thrombin activity in a whole blood sample, wherein said determined substance(s) is (are) added to the sample to be assayed or is (are) added during thrombin generation.

Substances that can be tested according to the method are for instance pharmaceuticals or other compounds having a coagulation effect on blood, such as coagulation factors or drugs or anticoagulant factors or drugs. Thrombin inhibitors can especially be tested according to the method of the invention.

In another aspect, the method of the invention can be used to screen substances in order to determine their capacity of interaction with thrombin activity.

According to the invention, the method which has been described above and which will be illustrated in the examples can be especially used for measurement of Endogenous Thrombin Potential (ETP) of the whole blood sample.

It can be also used for measurement of time to peak for thrombin or for measurement of clotting time.

It is also useful to measure the level of the peak of thrombin generated during the assay.

The method of the invention indeed allows the measurement of the so-called thrombin curve which is the first derivative of the measured fluorescence resulting from the reaction between thrombin and fluorogenic substrate.

In a particular method of the invention, a calibration step is performed such as the calibration described in the patent application WO 03/093831.

The method of the invention has been described in relation to the biological sample which is the whole blood sample. It could also be used to assay a sample which would be Platelet Rich Plasma (PRP) or even Platelet Poor Plasma (PPP).

The invention also relates to a kit for carrying out the method disclosed above and in the examples which follow wherein said kit comprises a fluorogenic substrate for thrombin,
tissue factor and calcium ions to enable thrombin generation,
optionally, a grid or microbeads that prevent retraction of blood clot and helps dispersion of the whole blood,
optionally a gel possibly comprising Calcium ions.

Optionally, the kit also comprises directions for use in order to provide specific guidance to carry out the method of the invention. Other features of the invention and advantageous thereof will be disclosed in the examples and in figures which follow.

LEGENDS OF THE FIGURES

FIG. 1: A Thrombogram Obtained from a subsampling experiment. The main features are: Lag time (=clotting time), peak height and area under the curve (=Endogenous Thrombin Potential, ETP).

FIG. 2: An example of thrombin generation curves obtained in platelet poor plasma by calibrated automated thrombinography.
AVK: Anti-Vitamin K treatment; TM: Thrombomodulin.

Figure 3:
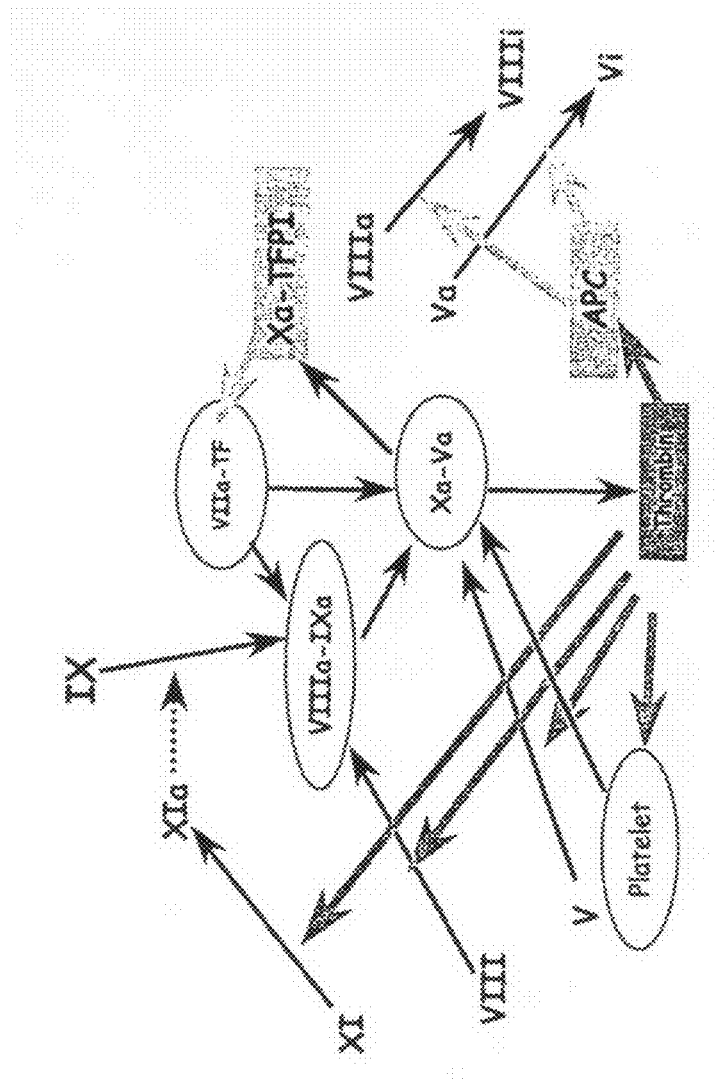

FIG. 3: A simplified scheme of thrombin formation: Positive and Negative feedbacks are apparent.

FIG. 4: Schematic representation of the effects of sedimentation and clot retraction on the fluorescent signal from clotting whole blood.
Legend: Larve ovals: Red blood cells
Starred circles: Fluorescent molecules that are exitated
Squares: Fluorescent molecules that are not exitated
Top horizontal (c.q. curved-) line: fluid surface
Bottom horizontal line: transparent bottom of measuring well
Stage A: Fluid blood just after filing of the well. (FIG. 1 t=0)
Stage B: Fluid blood just before clotting. (FIG. 1 t=B)
Stage C: Blood just after clotting. (FIG. 1 t=C)
Stage D: Blood after start of retraction. (FIG. 1 t=D)

Figure 5:
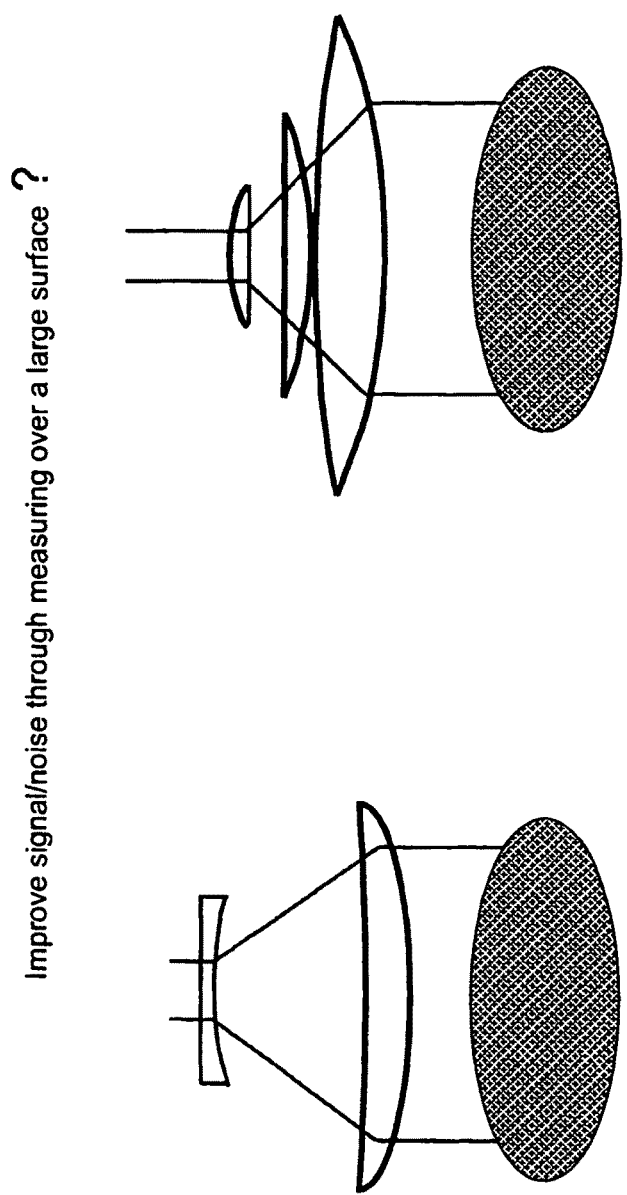

FIG. 5: Huygens eyepiece and condenser.

Figure 6:
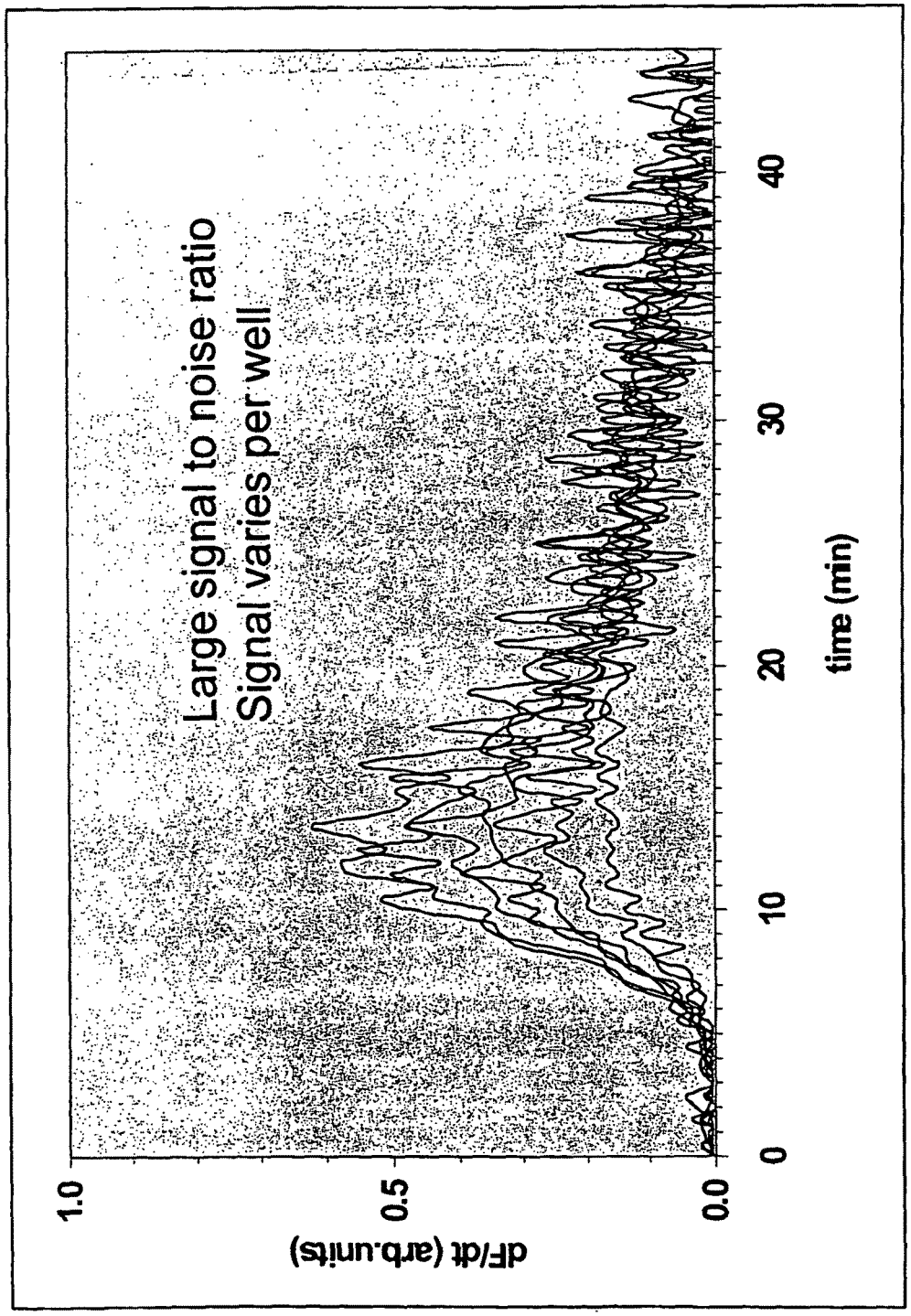

FIG. 6: Thin layer (3 mm) of blood in normal microtiter plate wells. Seven Identical experiments.

Figure 7:
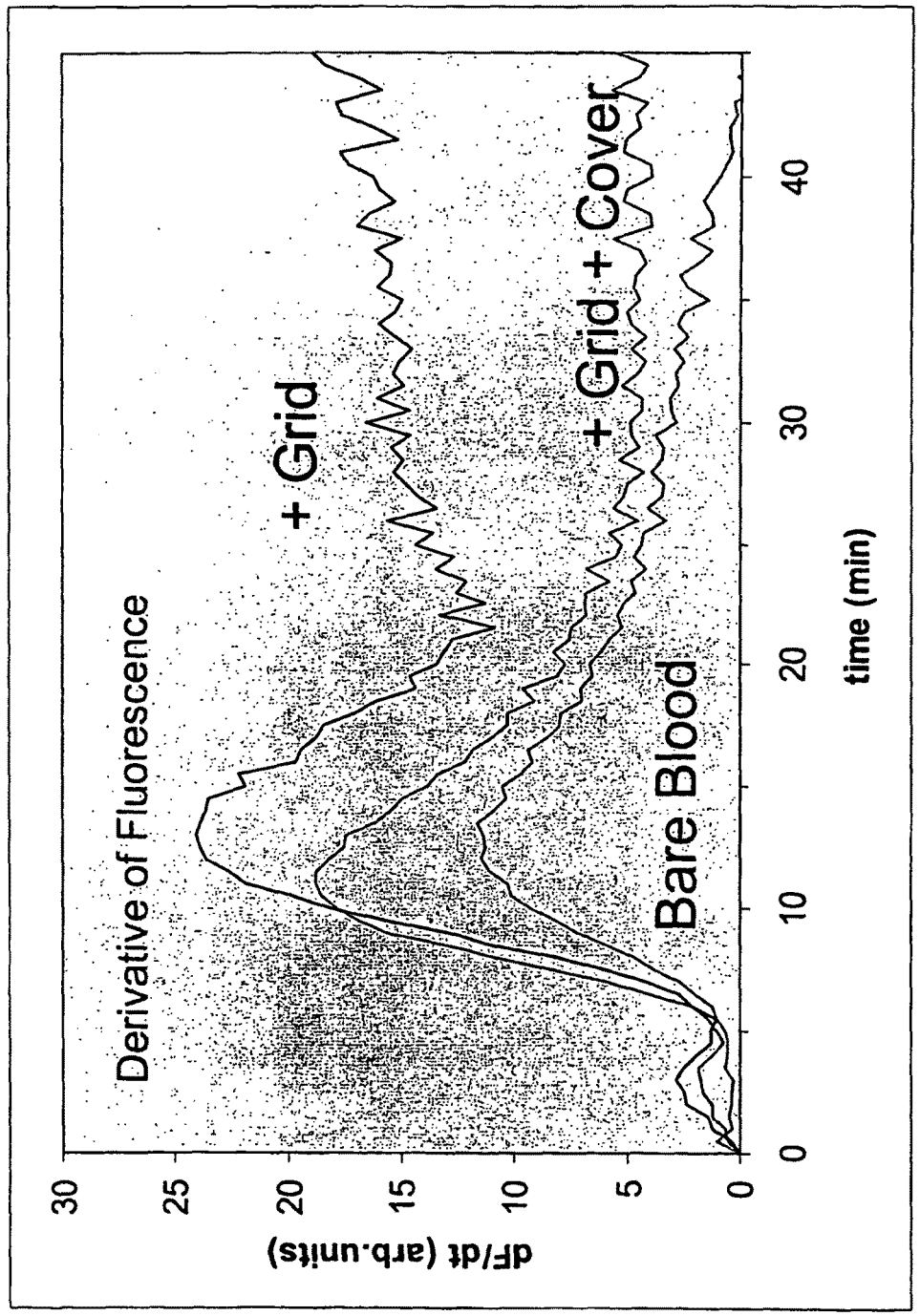

FIG. 7: Thin layer of blood in large surface microtiter plate wells.
32 lecture points per well Identical experiments.

Figure 8:
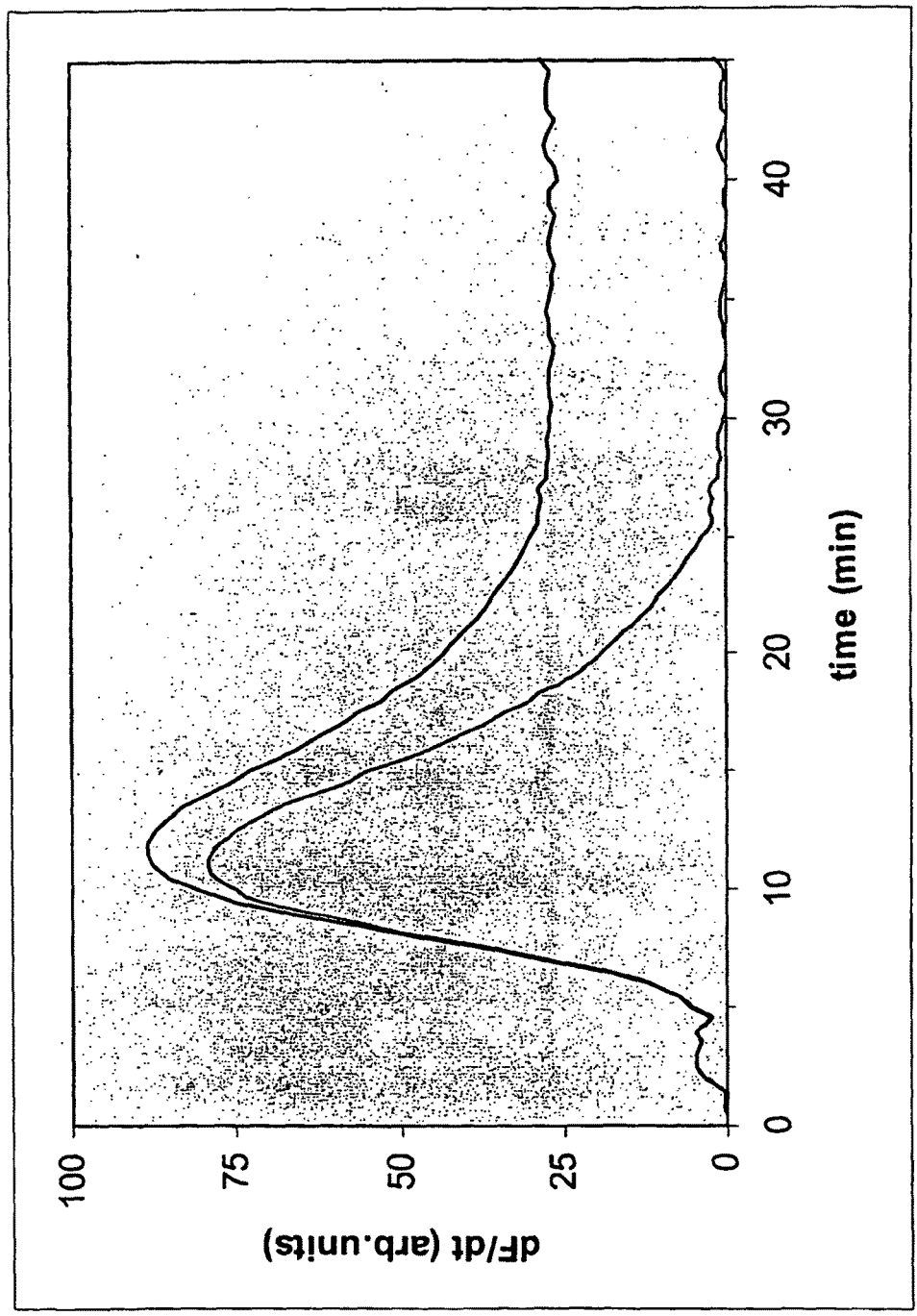

FIG. 8: Thin layer of blood in large surface microtiter plate well with mesh and cover. One lecture point through light collecting devise (Huygens eyepiece) (1) experimental curve, (2) after correction for α2M-thrombin.

Figure 9:
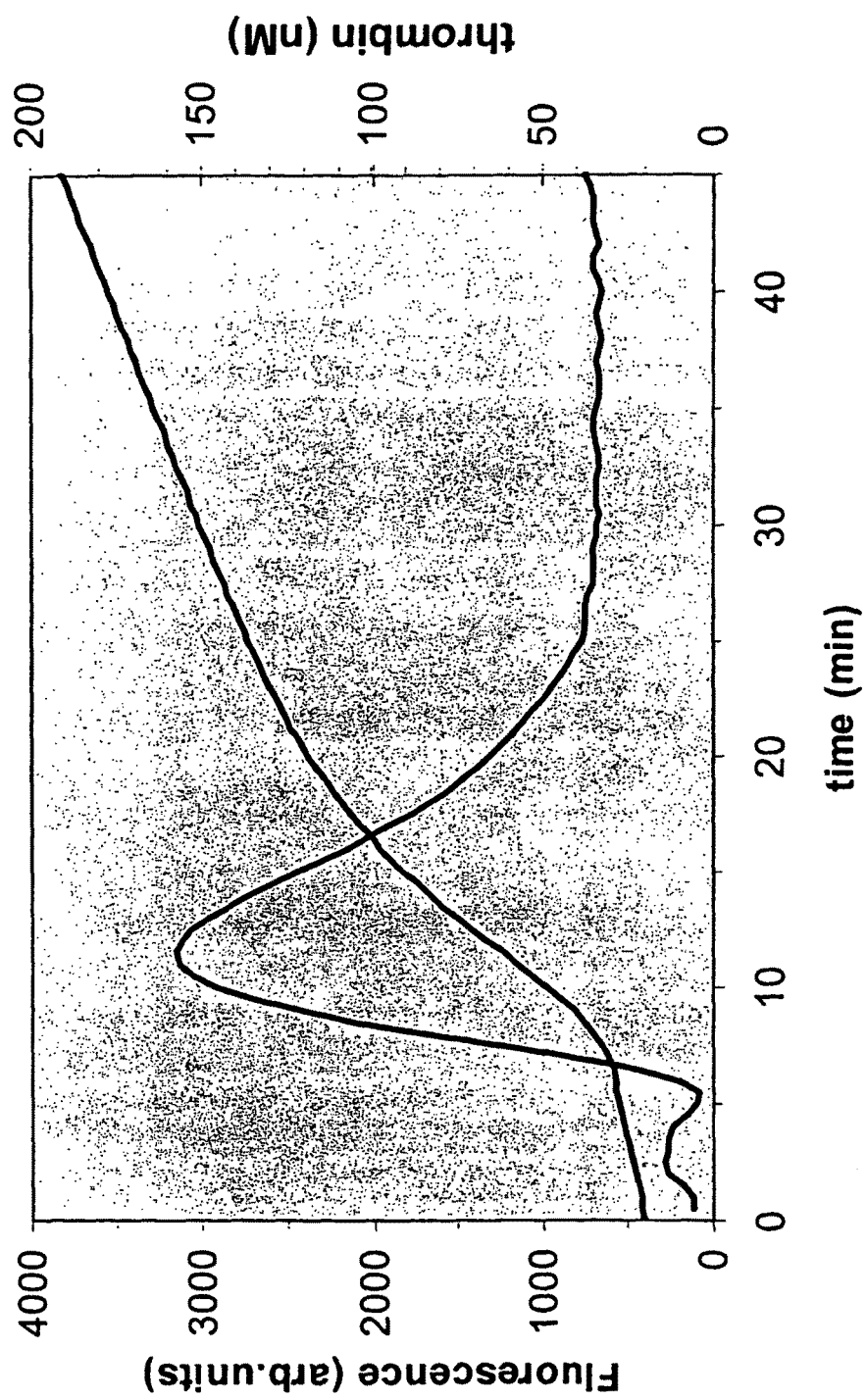

FIG. 9: From arbitrary units to thrombin.

Figure 10A:
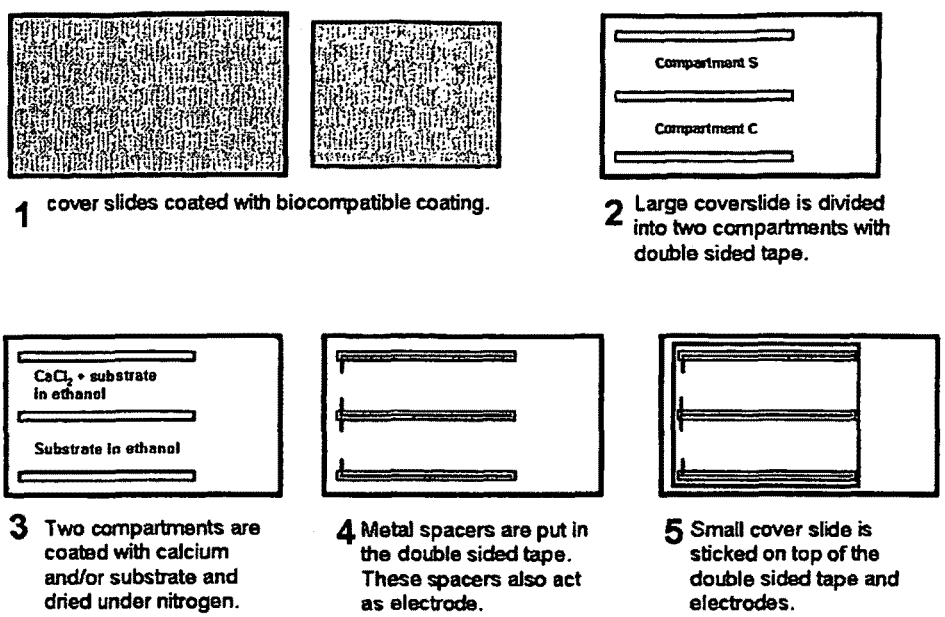

FIG. 10A: Sample cartridge design shows a possible design of a two-compartment measurement cartridge. One thin piece of (preferably rigid, e.g., glass) material (referred to as "slide") possibly coated with a biocompatible coating, is divided into compartments with a suitable spacer. This spacer may also act as electrode to detect sample injection by drop of resistance and/or increase of electric current. Each compartment may be coated with substances like calibrator and/or substrate (or any other needed substance like inhibitors and tissue factor). A second slide is attached on top of the other slide. Space between the two slides is 5-1000 μm, preferably 50 μm.

Figure 10B:
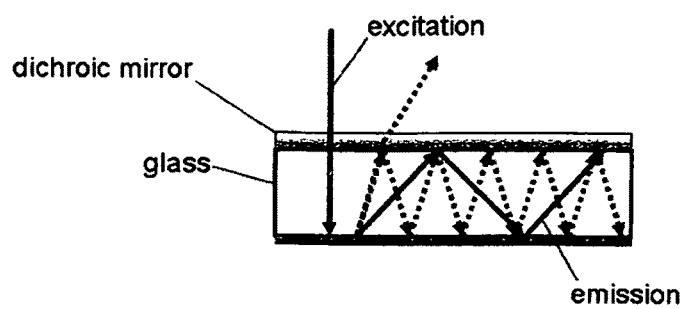

FIG. 10B: The path of the light when the cartridge is optionally coated on one or more sides by a suitable dichroic mirror coating enabling optical amplification. This allows the excitation light to enter the cartridge, while emission light is reflected within the cartridge and will be concentrated to a non-coated side of the cartridge.

Figure 11:
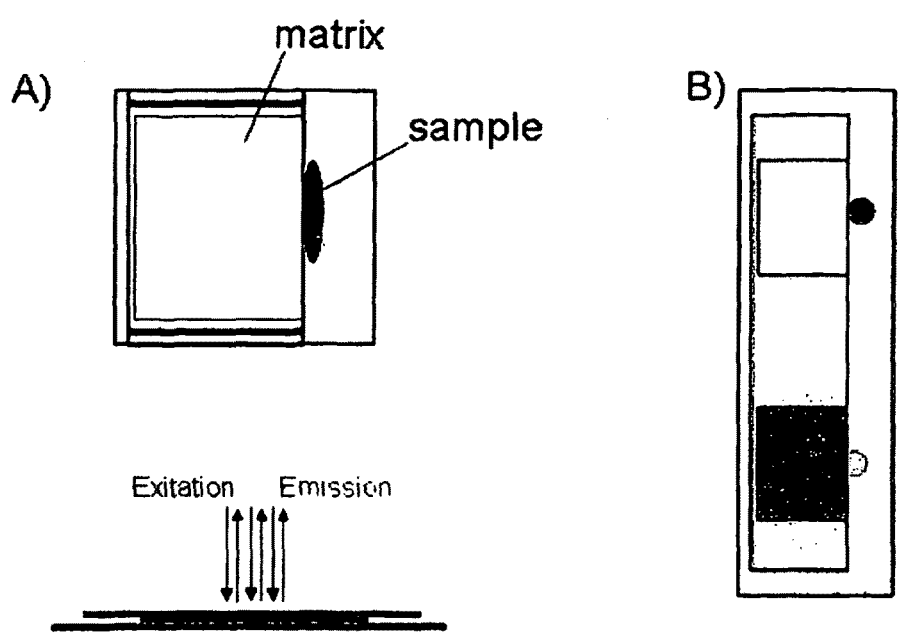

FIG. 11: Alternative cartridge design shows a piece of solid matrix, for example a porous polymer or cellulose, is put between two slides. This matrix may contain substrate and/or calcium (or any other substances like tissue factor, inhibitors). These substances may be present together with a solvent, in dried or lyophilized form.

FIG. 12 shows a TG curve measured in a thin layer of blood in a filter paper cell, converted to nM thrombin by a Staphylocoagulase calibrator.

EXAMPLES

I Measuring TG in Whole Blood: the Observed Phenomena and the Technical Difficulties for Measuring TG When a fluorogenic substrate is used, fluorescence can be provoked and measured only in so far as light is not intercepted by red blood cells, i.e., in the plasma space accessible to the excitation light, which is also the space from which the emitted light can be observed. For the sake of simplicity, we assume the red blood cells to be completely impenetrable to both types of light. If however to a certain extent RBC are penetrable, the reasoning needs not to be fundamentally altered.

Whole blood forms a clot at the end of the initiation phase, i.e., at the beginning of the explosive bulk of thrombin generation. In FIG. 4 four stages are depicted of the situation on the upper- and under-surfaces of blood, clotting in the well of a fluorimeter plate in the presence of a fluorogenic substrate and illuminated from the top or alternatively the bottom.

At stage A the stirred blood has just come to rest and the red blood cells are dispersed homogeneously in the fluid plasma (FIG. 4 A). In the course of the lag time before clotting (typically 3-12 minutes) sedimentation of the red blood cells takes place; at the top more plasma becomes accessible to light and less at the bottom (FIG. 4 B). As soon as blood clots (FIG. 4 C) the status quo raised in B is "frozen" by the appearance of the fibrin clot. Because of the action of thrombin on the blood platelets clot retraction sets in as soon as a clot is formed. Sedimentation and clot retraction are phenomena that are visible to the naked eye on a mm-per-hour scale. In the micrometer domain they occur in the course of minutes, i.e., in the time scale of the TG experiments. Retraction brings about an unequal distribution of the RBCs and also a change in the surface, such that it is no longer plane but becomes undulated. This undulation brings about an unequal repartition of plasma and clot at the surface and causes unpredictable optical effects. The surface irregularities are on a mm scale and visible to the naked eye. They therefore are of the same order of magnitude as the excitation light spot in normal fluorometry.

Sedimentation and retraction induce a change of the fluid volume in which fluorescent molecules can be reached by the excitation light. Due to this change the actual volume in which the measurement takes place is variable and unknown. Hence, reproducible quantification of the amount of thrombin from the rate of signal production obtained in these conditions is impossible, even if the effects of sedimentation and retraction would be negligible.

Experiments carried out by using ordinary microtiter plate wells and a volume that filled these wells to normal height (6 mm) allowed satisfactory results to be obtained only in a small percentage of all wells. This is explained by the fact that in ordinary fluorometry a sufficient signal is obtained only if the spot of surface measured (around 4 $mm^2$) coincides with an area where sufficient signal can be obtained because sufficient plasma is available; that is not above a retracted clot-mass but in a "valley" of the surface (see FIG. 4 D). The positive reports in the literature of measurement must result from a careful selection of the data obtained. In those cases where a signal of the right form is obtained, the quantitative measurement of thrombin is impossible because the measuring volume is unknown and variable. Measuring from the bottom through a transparent foil would solve the problem of surface irregularities but, due to the sedimentation of RBC, the signal becomes so small that it drowns in the background noise.

It has been observed that, with normal filling of the wells of a 96-well plate of the type available to date, it is possible to obtain an interpretable signal in 1 or 2 out of 10 wells. If the wells are filed to less than 2 mm height as the normally useful height, signal is obtained in near to all measurements. Nevertheless the signal that is obtained in this manner in a normal fluorimeter is very variable and small, i.e., corresponds to 1-5% of the signal obtained with plasma, and shows a large signal to noise ratio (FIG. 6). We concluded that there is no practical way to determine TG in whole blood using the optical setup of a normal fluorimeter.

II The Design of the Method of the Invention

1. Principle of the Invention

Unexpectedly it was found that (a) the effects of sedimentation and retraction progressively diminish with the thickness of the layer of clotting blood and, (b) that measuring fluorescence from a surface larger than around 10 $mm^2$ tends to equal out the remaining irregularities of the surface brought about by retraction. Equally unexpectedly, the effects of sedimentation and retraction can be further reduced by containing the blood in mazes or interstice, such as a filter grid (having mesh opening 50-500 µm) or packed spheres (diameter 50-500 µm). Consequently, the inventors provide conditions for obtaining an undisturbed fluorescent signal from the product of thrombin activity by enabling measurement to be carried out in a thin layer of blood (especially inferior to 2 mm) spread out over a surface larger than around 10 $mm^2$.

To solve the problem of the unknown volume in which the reaction is measured, the inventors further decided not to use pure substrate but rather substrate that already contained a fixed low, but known and readily measurable, concentration of fluorescent product.

2. Optical Device for Measurement

Measuring over a larger than normal surface requires optical devices that allow to illuminate the large surfaces and to collect the emitted light from that surface. One such device is not unlike a Huygens eyepiece, another like a microscope condenser (FIG. 5). To increase the fluorescent signal the blood can be spread on a reflecting surface, and such surface can be an integral part of the device described below.

3. The Device Containing the Blood Sample

The use of a device that contains the blood in the interstices of its structure allows simulation of the situation of blood shed in a wound, it can be made to contain tissue factor, thrombomodulin and or other elements known to exist in the normal vessel wall which affect the TG process (e.g. collagen). For the sake of comparison the material from which the device is made can be chosen among inert material such as e.g. nylon or polypropylene.

To prevent drying out of the surface, the thin layer of blood can be covered by a thin film of solid or fluid material. Alternatively the blood can be guided into a slit within a translucent material, e.g. by capillary force.

4. Measurement

It is an advantage of measuring in a thin layer that the fluorescent signal is proportional to the concentration of fluorescent molecules; in other words, the inner filter effect does not play a role. Substrate consumption does play a role however. It can be compensated for in three ways: (a) As in the chromogenic method (38), i.e. by providing substrates with kinetic constants such that substrate consumption has a negligible effect, (b) By correcting for substrate consumption mathematically, i.e. by applying the integrated rate equation and (c) By using a calibrator as described in patent WO 03/093831.

The course of thrombin concentration in clotting whole blood is determined from the enzymatic action of thrombin on a fluorogenic substrate added to the blood. A stable and sufficient signal has been obtained by measuring in a thin layer illustrated by a layer of less than 2 mm of thickness over a large surface (illustrated by a surface having more than 10 $mm^2$). To measure the actual volume in which the reaction takes place a small amount of fluorophore is added to the substrate. A specialized optical device is required for illuminating the whole of the surface and another for collecting the light emitted from the surface.

The thin layer could be stabilized and prevented from drying by a series of mechanical means, among which an inert grid or a grid of material chosen such as to imitate certain properties of the vessel wall. Alternatively a small slit can be used.

The setup can also be used for measuring thrombin generation in platelet poor and platelet rich plasma.

5. Reaction Mixture

Chemicals

Recombinant relipidated tissue factor (rTF) not containing polybrene or $Ca^{++}$ is from Dade Behring (Marburg, Germany). Fluorogenic substrate, Z-Gly-Gly-Arg-AMC is obtained from Bachem (Switzerland). Upon splitting by thrombin it releases the fluorescent 7-amino-4-methylcoumarine (AMC) which is measured by a 390 nm excitation and a 460 nm emission filter set.

A fresh mixture of fluorogenic substrate and $CaCl_2$ (FluCa) is prepared for each experiment as follows: to 875 µL of Buffer (Hepes 20 mM, pH 7.35) containing 60 g/L BSA (Sigma, A-7030) 100 µL of 1 M $CaCl_2$ was added. At 37° C., 25 µL of a 100 mM DMSO-solution of the fluorogenic substrate was squirted in and immediately vigorously mixed. The resulting clear solution, referred to as FluCa, thus is 2.5 mM in fluorogenic substrate and 100 mM in $CaCl_2$.

Buffer A contains 20 mM hepes, 140 mM NaCl, 5 mg/ml BSA, pH=7.35. Buffer B contains 20 mM hepes, 140 mM NaCl, 60 mg/ml, pH=7.35

Blood and Plasma

Blood is obtained through venapuncture (1 volume trisodium citrate 0.13 M to 9 volumes blood). Free flow or minimal suction should be employed; vacuum containers are to be avoided.

The measurements are carried out in a plate fluorimeter (Ascent reader, Thermolabsystems OY, Helsinki Finland) equipped with a 390/460 filter set (excitation/emission). Instead of a normal 96 well plate, a well plate is used with 24 round wells with a diameter of 15 mm and hence a surface of 175 $mm^2$. The wells are prepared by washing several times with buffer A and drying the wells.

Then the mixture of blood and substrate is added in which thrombin generation takes place. This mixture contains, per well to be filled: 80 µL citrated whole blood, 20 µL Innovin® 1:1000 diluted in buffer A, 20 µL FluCa or, as the case be, a multiple of these volumes.

Immediately after addition of the FluCa, the mixture is stirred on a Vortex mixer and added to the wells. The plate is inserted into the fluorimeter and shaken during 10 s. at 1200 rpm and then measured every two minutes at 390/460 nm 37° C. during an hour.

To each well 120 µL of the mixture is added.

Example 1

Multiple Lecture Points, Adding a Mesh and a Cover

Thrombin generation was triggered as indicated above in three wells. Per well 24 spots were illuminated and measured one after the other. The signals from the 24 points at each reading were added. The results are shown in FIG. 7. It is seen that the signal is augmented and stabilized by adding a grid, here a nylon filter with a 600 µM mesh opening, 51% open area and a thickness of 445 µM (Spectrum Laboratories Inc. Rancho Dominguez Calif., USA). However, the signal spuriously increases with time due to evaporation and concentration of the top layer. This is prevented by covering with a plastic foil. (Thermosprint optical clean sealing tape for QPCR (Bilatec AG, Mannheim, Germany).

Example 2

Multiple Lecture Points, Adding a Gel and a Cover

Thrombin generation was triggered as indicated above in three wells. Per well 24 spots were illuminated and measured one after the other. The signals from the 24 points at each reading were added. To two wells 700 µL of a 50% (v/v) Spehadex-25 in 150 mM NaCl solution is added and the powder is allowed to settle for 5 minutes. The supernatant (300-400 µL) is removed from the well with a pipette.

Then 120 µL of the clotting blood mixture is added. On top of one of these two wells a plastic foil. (Thermosprint optical clean sealing tape for QPCR (Bilatec AG, Mannheim, Germany) was applied. The results are comparable to those in FIG. 7

Example 3

The Light with an Optical Device

For this experiment one well, with grid and cover as in example 1, was measured with the aid of a Fluostar optima fluorimeter (BMG Labtech, Offenburg, Germany). The light from the sample was collected into a Huygens eyepiece (10× magnification) and read after passing through this optical device. The results are shown in FIG. 8

Example 4

From Arbitrary Units to Thrombin

This experiment was essentially carried out as that in example 1 with mesh and cover but a known amount (10 nM) of AMC was added to the substrate Z-Gly-Gly-Arg-AMC. Due to sedimentation of the erythrocytes, the volume in which the measurement takes place increases so the signal from the AMC present increases. At the moment of coagulation the situation "freezes" and no further sedimentation takes place. At that moment, known from a sudden increase in signal, we measure the amount of fluorescence due to the 10 nM of AMC added. In this way we know how to convert units of fluorescence (F) in concentration of AMC. Thus the dF/dt measured can be converted into d[AMC]/dt. From an independent experiment we know what d[AMC]/dt corresponds to what thrombin concentration. Thus the velocity of change of the fluorescence (FIG. 9, black line) can be converted into concentration of thrombin in the sample.

Example 5

Device Containing the Blood Sample

A filter paper cell containing substrate and $Ca^{2+}$-ions is prepared by adding 50 µL of a 100 mM DMSO-solution of the fluorogenic substrate and 100 µL of a 1 M $CaCl_2$ solution to 5850 µL ethanol. 11 µL of this solution is spread on a piece of solid matrix (Whatman 1 mM chromatography paper) of 7×9 mm and dried under nitrogen. Next it is covered between to pieces of plastic (Thermosprint optical clean sealing tape for QPCR, Bilatec AG, Mannheim, Germany) as shown in FIG. 11.

The same procedure is used to prepare a filter paper cell only containing substrate, in this case, 50 µL of a 100 mM DMSO solution of the fluorogenic substrate is added to 5950 µL ethanol, of which 11 µL is spread on a piece of solid matrix and dried under nitrogen.

Multiple Lecture Points, Using a Filter Paper Cell.

Two filter paper cells, one containing fluorogenic substrate and calcium ions (A) and one only containing substrate (B) were freshly prepared as described above.

A 4:1:1 mixture of citrated whole blood, buffer B and Innovin® (1:1000 diluted in buffer A) was prepared. As a calibrator, a 4:1:1 mixture of citrated whole blood, polymerization inhibitor (H-Gly-Pro-Arg-Pro-OH AcOH) (Bachem feinchemikalien AG, Bubendorf, Switserland) in buffer B (1.0 mM) and 20 µM staphylocoagulase was prepared by mixing whole blood and polymerization inhibitor. Just before starting the experiment, the Staphylocoagulase was added and the sample was mixed well.

Immediately after adding the Staphylocoagulase, the experiment is started by adding 11 µL of the TG sample to cell A and 11 µL of the calibrator to cell B. This is done by pipetting the drops close to the solid matrix in a way that the drop touches the matrix (see FIG. 11) and is sucked into it by capillary forces. Per cell, 4 spots are illuminated and measured one after the other.

The signal from the calibrator is a straight line, the slope is used to convert the signal from the sample cell into nM thrombin. This is conventional signal calibration as known to the art and not continuous calibration in the sense of patent application PCT/EP 03/04705. Results are shown in FIG. 12.

REFERENCES

1. Loeliger E A. The optimal therapeutic range in oral anticoagulation. History and proposal. *Thromb Haemost* 1979; 42:1141-52.
2. A double-blind trial to assess long-term oral anticoagulant therapy in elderly patients after myocardial infarction. Report of the Sixty Plus Reinfarction Study Research Group. *Lancet* 1980; 2:989-94.
3. Engelberg H. Heparin and atherosclerosis. A review of old and recent findings. *Am Heart J* 1980; 99:359-72.
4. Marongiu F, Biondi G, Sorano G G, Mameli G, Conti M, Mamusa A M, Cadoni M C, Balestrieri A. Bleeding time is prolonged during oral anticoagulant therapy. *Thromb Res* 1990; 59:905-12.
5. Schulman S, Johnsson H. Heparin, DDAVP and the bleeding time. *Thromb Haemost* 1991; 65:242-4.
6. Sjolin K E. The thrombin generation test in the diagnosis of classical hemophilia and Christmas disease. *Scand J Clin Lab Invest* 1956; 8:138-44.
7. Peyrou V, Lormeau J C, Herault J P, Gaich C, Pfliegger A M, Herbert J M. Contribution of erythrocytes to thrombin generation in whole blood. *Thromb Haemost* 1999; 81:400-6.
8. Giesen P L, Nemerson Y. Tissue factor on the loose. *Semin Thromb Hemost* 2000; 26:379-84.
9. Giesen P L, Rauch U, Bohrmann B, Kling D, Roque M, Fallon J T, Badimon J J, Himber J, Riederer M A, Nemerson Y. Blood-borne tissue factor: another view of thrombosis. *Proc Natl Acad Sci USA* 1999; 96:2311-5.
10. Hemker H C. Platelet procoagulant activities: the amplification loops between platelets and the plasmaticclotting system. In *Platelets, Gresele, Page and Fuster edts.* 2002; Cambridge University Press:381-392.
11. Beguin S, Keularts I, Al Dieri R R, Bellucci S, Caen J, Hemker H C. Fibrin polymerization is crucial for thrombin generation in platelet-rich plasma in a VWF-GPlb-dependent process, defective in Bernard-Soulier syndrome. *J Thromb Haemost* 2004; 2:170-6.
12. Beguin S, Kumar R, Keularts I, Seligsohn U, Coller B S, Hemker H C. Fibrin-dependent platelet procoagulant activity requires GPlb receptors and von Willebrand factor. *Blood* 1999; 93:564-70.
13. Kessels H, Beguin S, Andree H, Hemker H C. Measurement of thrombin generation in whole blood—the effect of heparin and aspirin. *Thromb Haemost* 1994; 72:78-83.
14. Reverter J C, Beguin S, Kessels H, Kumar R, Hemker H C, Coller B S. Inhibition of platelet-mediated, tissue factor-induced thrombin generation by the mouse/human chimeric 7E3 antibody. Potential implications for the effect of c7E3 Fab treatment on acute thrombosis and "clinical restenosis". *J Clin Invest* 1996; 98:863-74.
15. Keularts I M, Beguin S, de Zwaan C, Hemker H C. Treatment with a GPIIb/IIIa antagonist inhibits thrombin generation in platelet rich plasma from patients. *Thromb Haemost* 1998; 80:370-1.
16. Herault J P, Dol F, Gaich C, Bemat A, Herbert J M. Effect of clopidogrel on thrombin generation in platelet-rich plasma in the rat. *Thromb Haemost* 1999; 81:957-60.
17. Prevention of pulmonary embolism and deep vein thrombosis with low dose aspirin: Pulmonary Embolism Prevention (PEP) trial. *Lancet* 2000; 355: 1295-302.
18. Rotteveel R C, Roozendaal K J, Eijsman L, Hemker H C. The influence of oral contraceptives on the time-integral of thrombin generation (thrombin potential). *Thromb Haemost* 1993; 70:959-62.
19. Rosing J, Hemker H C, Tans G. Molecular biology and pathophysiology of APC resistance: current insights and clinical implications. *Semin Thromb Hemost* 1998; 24:329-35.
20. Regnault V, Beguin S, Wahl D, de Maistre E, Coenraad Hemker H, Lecompte T. Thrombinography shows acquired resistance to activated protein C in patients with lupus anticoagulants. *Thromb Haemost* 2003; 89:208-12.
21. Redondo M, Watzke H H, Stucki B, Sulzer I, Biasiutti F D, Binder B R, Furlan M, Lammle B, Wuillemin W A. Coagulation factors II, V, VII, and X, prothrombin gene 20210G-> A transition, and factor V Leiden in coronary artery disease: high factor V clotting activity is an independent risk factor for myocardial infarction. *Arterioscler Thromb Vasc Biol* 1999; 19:1020-5.
22. Burzotta F, Leone A M, Paciaroni K, De Stefano V, Rossi E, Testa L, Giannico F, Leone G, Maseri A, Crea F, Andreotti F. G20210A prothrombin gene variant and clinical outcome in patients with a first acute coronary syndrome. *Haematologica* 2004; 89:1134-8.
23. Burzotta F, Paciaroni K, De Stefano V, Crea F, Maseri A, Leone G, Andreotti F. G20210A prothrombin gene polymorphism and coronary ischaemic syndromes: a phenotype-specific meta-analysis of 12 034 subjects. *Heart* 2004; 90:82-6.
24. French J K, Van de Water N S, Sutton T M, Lund M, Gao W, McDowell J, Liu-Stratton Y, Pohorence J, Szymanski D, Goldschmidt-Clermont P, White H D, Browett P J, Cooke G. Potential thrombophilic mutations/polymorphisms in patients with no flow-limiting stenosis after myocardial infarction. *Am Heart J* 2003; 145:118-24.
25. Thompson S G, Kienast J, Pyke S D, Haverkate F, van de Loo J C. Hemostatic factors and the risk of myocardial infarction or sudden death in patients with angina pectoris. European Concerted Action on Thrombosis and Disabilities Angina Pectoris Study Group. *N Engl J Med* 1995; 332:635-41.
26. Soskin P, Wiesel M L, Mossard J M, Arbogast R, Najib K, Grunebaum L, Sacrez A, Cazenave J P. [Von Willebrand factor in coronary disease]. *Arch Mal Coeur Vaiss* 1994; 87:85-93.
27. Faber C G, Lodder J, Kessels F, Troost J. Thrombin generation in platelet-rich plasma as a tool for the detection of hypercoagulability in young stroke patients. *Pathophysiol Haemost Thromb* 2003; 33:52-8.
28. Siegemund T, Petros S, Siegemund A, Scholz U, Engelmann L. Thrombin generation in severe haemophilia A and B: the endogenous thrombin potential in platelet-rich plasma. *Thromb Haemost* 2003; 90:781-6.
29. Siegemund A, Petros S, Siegemund T, Scholz U, Seyfarth H J, Engelmann L. The endogenous thrombin potential and high levels of coagulation factor VIII, factor IX and factor XI. *Blood Coagul Fibrinolysis* 2004; 15:241-4.
30. Keularts I M, Zivelin A, Seligsohn U, Hemker H C, Beguin S. The role of factor XI in thrombin generation induced by low concentrations of tissue factor. *Thromb Haemost* 2001; 85:1060-5.
31. Keularts I M, Hamulyak K, Hemker H C, Beguin S. The effect of DDAVP infusion on thrombin generation in platelet-rich plasma of von Willebrand type 1 and in mild haemophilia A patients. *Thromb Haemost* 2000; 84:638-42.
32. Al Dieri R, Peyvandi F, Santagostino E, Giansily M, Mannucci P M, Schved J F, Beguin S, Hemker H C. The thrombogram in rare inherited coagulation disorders: its relation to clinical bleeding. *Thromb Haemost* 2002; 88:576-82.
33. Hemker H C, Beguin S. Phenotyping the clotting system. *Thromb Haemost* 2000; 84:747-51.
34. Kessels H, Kester A D, Hemker H C. Intrinsic and method-induced variation of the bleeding time and related parameters. *Thromb Haemost* 1994; 71:798-9.
35. Biggs R, Mac F R. The reaction of haemophilic plasma to thromboplastin. *J Clin Pathol* 1951; 4:445-59.
36. Biggs R, Douglas A S, Macfarlane R G. The formation of thromboplastin in human blood. *J Physiol* 1953; 119:89-101.
37. Macfarlane R G, Biggs R. A thrombin generation test; the application in haemophilia and thrombocytopenia. *J Clin Pathol* 1953; 6:3-8.
38. Hemker H C, Wielders S, Kessels H, Beguin S. Continuous registration of thrombin generation in plasma, its use for the determination of the thrombin potential. *Thromb Haemost* 1993; 70:617-24.
39. Hemker H C, Giesen P L, Ramjee M, Wagenvoord R, Beguin S. The thrombogram: monitoring thrombin generation in platelet-rich plasma. *Thromb Haemost* 2000; 83:589-91.
40. Hemker H C, Giesen P, AlDieri R, Regnault V, de Smed E, Wagenvoord R, Lecompte T, Beguin S. The calibrated automated thrombogram (CAT): a universal routine test for hyper- and hypocoagulability. *Pathophysiol Haemost Thromb* 2002; 32:249-53.
41. Hemker H C, Giesen P, Al Dieri R, Regnault V, de Smedt E, Wagenvoord R, Lecompte T, Beguin S. Calibrated automated thrombin generation measurement in clotting plasma. *Pathophysiol Haemost Thromb* 2003; 33:4-15.
42. Hemker H C, Beguin S. Thrombin generation in plasma: its assessment via the endogenous thrombin potential. *Thromb Haemost* 1995; 74:134-8.
43. Hemker H C, Al Dieri R, Beguin S. Thrombin generation assays: accruing clinical relevance. *Curr Opin Hematol* 2004; 11:170-5.
44. Ramjee M K. The use of fluorogenic substrates to monitor thrombin generation for the analysis of plasma and whole blood coagulation. Anal *Biochem* 2000; 277:11-8.
45. Lo K, Diamond S L. Blood coagulation kinetics: high throughput method for real-time reaction monitoring. *Thromb Haemost* 2004; 92:874-82.

The invention claimed is:

1. A method for in vitro determining thrombin activity in a biological sample which is a sample of whole blood or a plasma sample and wherein thrombin generation is measured by the steps of:
    contacting a layer of said sample with a fluorogenic substrate of thrombin, wherein said layer has a thickness within a range of about 0.05 to about 5 mm and a surface within a range of about 10 to 500 mm$^2$ and wherein said sample is put into contact with a filter grid having a mesh size of about 50 to about 500 microns or packed spheres having a diameter of about 50 to about 500 microns which helps dispersion of the sample whereby sedimentation of the sample and retraction of the clot are decreased,
    allowing thrombin to generate in said sample, wherein said filter grid or packed spheres maintains the homogeneous dispersion of the sample after thrombin activation while reducing sedimentation of the sample and retraction of the clot within the assayed sample; and
    measuring the fluorescence emitted from the surface of the layer, by the fluorescent group released from the fluorogenic substrate as a result of enzymatic action of generated thrombin on said fluorogenic substrate.

2. The method of claim 1, wherein the concentration of thrombin generated during the assay is determined as a function of the measured fluorescence of the released fluorescent group.

3. The method of claim 1, wherein the whole blood sample is diluted within a range of maximum 10 times.

4. The method according to claim 1, wherein the thickness of the layer of the sample is about 2 mm or less.

5. The method according to claim 1, wherein the well containing the blood sample is covered for the determination of thrombin activity.

6. The method according to claim 1, wherein a fluorophore is added to the fluorogenic substrate of thrombin wherein the respective proportions of added fluorophore is in the range of 1 to 10% of the quantity of fluorescent molecule bound to thrombin substrate.

7. The method according to claim 1, wherein the amount of thrombin substrate added to the sample is within a range of 50 to 1000 μM.

8. The method according to claim 1, wherein the fluorogenic substrate is a synthetic substrate for thrombin, coupled with a fluorescent molecule.

9. The method according to claim 8, wherein the thrombin substrate is an organic chemical compound coupled with a fluorescent molecule.

10. The method according to claim 9, wherein the fluorogenic substrate is an oligopeptide having a sequence of 2 to 30 amino acid residues coupled with a fluorescent molecule.

11. The method according to claim 10, wherein the oligopeptide has a terminal lysine or arginine for coupling with a fluorescent molecule.

12. The method according to claim 8, wherein the fluorescent molecule is AMC (7-amino-4-methylcoumarin).

13. The method according to claim 1, wherein the well further comprises a gel, wherein said gel does not enable dilution of the blood of the sample.

14. The method according to claim 13, wherein the gel contains calcium ions.

15. The method according to claim 1, wherein tissue factor and Calcium ions are added to the blood sample in quantities enabling thrombin generation to occur.

16. The method according to claim 1, wherein the blood sample is a sample of whole blood.

17. The method according to claim 16 wherein the sample of whole blood is citrated.

18. The method according to claim 1, wherein the blood sample is a sample of plasma.

19. The method according to claim 18, wherein the blood sample is a sample of Platelet Rich Plasma (PRP).

20. The method according to claim 1, further comprising a step of measurement of Endogenous Thrombin Potential (ETP) of the whole blood sample.

21. The method according to claim 1, further comprising a step of measurement of time to peak of thrombin.

22. The method according to claim 1, further comprising a step of measurement of clotting time.

23. The method according to claim 1, further comprising a step of measurement of the level of the peak of thrombin generated.

24. The method according to claim 1, which further comprises a calibration step.

25. A process for detecting or monitoring a disease comprising the steps of:
 a) measuring thrombin generation in a biological sample which is a sample of whole blood or a plasma sample wherein thrombin generation is measured by the steps of:
  contacting a layer of said sample with a fluorogenic substrate of thrombin, wherein said layer has a thickness within a range of about 0.05 to about 5 mm and a surface within a range of about 10 to about 500 mm$^2$; wherein said sample is put into contact with a filter grid having a mesh size of about 50 to about 500 microns or packed spheres having a diameter of about 50 to about 500 microns, which helps dispersion of the sample, whereby sedimentation of the sample and retraction of the clot are decreased
  allowing thrombin to generate in said sample, wherein said filter grid of packed spheres maintains the homogeneous dispersion of the sample after thrombin activation while reducing sedimentation of the sample and retraction of the clot within the assayed sample; and
  measuring the fluorescence emitted from the surface of the layer, by the fluorescent group released from the fluorogenic substrate as a result of enzymatic action of generated thrombin on said fluorogenic substrate,
 b) detecting or monitoring a haemostatic disease or a thrombotic disease.

26. The process according to claim 25, wherein the measurement of thrombin generation in step a) or the detection or monitoring of a haemostatic disease or a thrombotic disease in step b) includes a step of adding determined substance(s) added to the sample to be assayed, said process further comprising a step of detecting or monitoring the interaction said determined substance(s) on thrombin activity in a whole blood sample.

27. The process according to claim 25, further comprising a step of monitoring interaction of coagulation factors or drugs.

28. The process according to claim 25, further comprising a step of screening substances to determine their interacting capacity with thrombin generation.

* * * * *